United States Patent
Xie et al.

(10) Patent No.: US 10,400,279 B2
(45) Date of Patent: Sep. 3, 2019

(54) METHOD FOR CONSTRUCTING A SEQUENCING LIBRARY BASED ON A SINGLE-STRANDED DNA MOLECULE AND APPLICATION THEREOF

(71) Applicants: Tsinghua University, Beijing (CN); Singapore Institute for Clinical Sciences, A-STAR, Singapore (SG)

(72) Inventors: Wei Xie, Beijing (CN); Qiangzong Yin, Beijing (CN); Jingyi Wu, Beijing (CN); Feng Xu, Beijing (CN); Xu Peng, Beijing (CN)

(73) Assignees: TSINGHUA UNIVERSITY, Beijing (CN); SINGAPORE INSTITUTE FOR CLINICAL SCIENCES, A-STAR, Singapore (SG)

( * ) Notice: Subject to any disclaimer, the term of this patent is extended or adjusted under 35 U.S.C. 154(b) by 236 days.

(21) Appl. No.: 15/503,428

(22) PCT Filed: Aug. 31, 2015

(86) PCT No.: PCT/CN2015/088680
§ 371 (c)(1),
(2) Date: Feb. 13, 2017

(87) PCT Pub. No.: WO2016/037537
PCT Pub. Date: Mar. 17, 2016

(65) Prior Publication Data
US 2017/0226582 A1    Aug. 10, 2017

(30) Foreign Application Priority Data

Sep. 12, 2014  (CN) .......................... 2014 1 0466261

(51) Int. Cl.
*C12Q 1/6874*  (2018.01)
*C12N 15/10*  (2006.01)
*C12Q 1/6806*  (2018.01)
*C40B 50/06*  (2006.01)

(52) U.S. Cl.
CPC ....... *C12Q 1/6874* (2013.01); *C12N 15/1093* (2013.01); *C12N 15/1096* (2013.01); *C12Q 1/6806* (2013.01); *C40B 50/06* (2013.01)

(58) Field of Classification Search
None
See application file for complete search history.

(56) References Cited

U.S. PATENT DOCUMENTS

2010/0035249 A1  2/2010 Hayashizaki et al.
2012/0157343 A1  6/2012 Shafer

FOREIGN PATENT DOCUMENTS

WO        2004081225 A2    9/2004
WO   WO-2004081225 A2 *  9/2004  ............. C12N 15/10

OTHER PUBLICATIONS

Chen et al., "Molecular characterization of the full-length L and M RNAs of Tomato yellow ring virus, a member of the genus *Tospovirus*," Virus Genes 2013, 46:487-495. (Year: 2013).*
Weber et al., "Chromosome-wide and promoter-specific analyses identify sites of differential DNA methylation in normal and transformed human cells," Nature Genetics 2005, 37:853-862. (Year: 2005).*
Li et al., "Complete genomic sequence of watermelon bud necrosis virus," Arch Virol, 2011, vol. 156, pp. 359-362.
Kanagawa, "Bias and Artifacts in Multitemplate Polymerase Chain Reactions (PCR)," Journal of Bioscience and Bioengineering, 2003, vol. 96, No. 4, pp. 317-323.
Lister et al., "Human DNA methylomes at base resolution show widespread epigenomic differences," Nature, Nov. 19, 2009, vol. 462, pp. 315-322.

* cited by examiner

*Primary Examiner* — Kaijiang Zhang
(74) *Attorney, Agent, or Firm* — Hodgson Russ LLP

(57) ABSTRACT

A method for constructing a sequencing library based on a single-stranded DNA molecule is provided comprising: (1) forming a poly(C)n tail at a 3'-terminus of the single-stranded DNA molecule, to obtain a single-stranded DNA molecule with the poly(C)n tail with n representing a number of base C, and n being an integer ranging from 5 to 30; (2) obtaining a double-stranded DNA molecule by using an extension primer based on the single-stranded DNA molecule with the poly(C)n tail, with the extension primer comprising a H(G)m unit at a 3'-terminus thereof, H being base A, base T or base C, m being a number of base G, and m being an integer ranging from 5 to 15; and (3) ligating an adapter to one terminus of the double-stranded DNA molecule remote from the H(G)m unit, and amplifying the resulting ligation product to obtain an amplification product forming the sequencing library.

18 Claims, 7 Drawing Sheets

Specification includes a Sequence Listing.

Library structure obtained after the first round of PCR amplified a whole library

METHOD FOR CONSTRUCTING A SEQUENCING LIBRARY BASED ON A SINGLE-STRANDED DNA MOLECULE AND APPLICATION THEREOF

CROSS-REFERENCE TO RELATED APPLICATION

This application is the U.S. national phase of PCT Application No. PCT/CN2015/088680 filed on Aug. 31, 2015, which claims a priority to and benefits of Chinese Patent Application Serial No. 201410466261.2, filed with the State Intellectual Property Office of P. R. China on Sep. 12, 2014, the entire contents of which are incorporated herein by reference.

FIELD

The present invention relates to biotechnology, especially to gene sequencing. Specifically the present invention relates to method and application for constructing a sequencing library based on a single-stranded DNA molecule. More specifically, the present invention relates to method for constructing a sequencing library based on a single-stranded DNA molecule, apparatus for constructing a sequencing library based on a single-stranded DNA molecule, method for determining a sequence information of a single-stranded DNA molecule, method for determining a sequence data of a RNA sample, method for determining a sequence data of a target region in a chromatin and method for determining a methylation information in a genome.

BACKGROUND

With the rapid progress of the second generation sequencing technology, normal and pathogenic genes of human and animal are analyzed and identified. Unknown problems of biogenetics and auxology are understood on whole genome level. It is indispensable step before gene sequencing to set up library of standard sample suitable to the second generation sequencing plat, which is named library construction in brief. The main methods of library construction now are Trueseq and Nextera systems from Illumia, which are both complicated on operation. During operation of the both, it is necessary to end blunting, adding base A and ligating adapter to one terminus, which are all needed to be operated in purified sample system, as a result every step must has purified operation. While as technological limitation, it is inevitable to have some sample loss for purified operation, which result in large beginning amount of DNA, at least nanogram level, and a huge amount of information loss during library construction. For trace sample, such as scarce sample or sample from clinical patients, traditional library construction methods are not suitable. In conclusion, there should have some improvements on gene library construction methods of the second generation sequencing technology.

SUMMARY

The aim of the present invention is to solve at least one of the technical problems of the prior art. As a result, one aspect of the present invention are to provide a kind of easy-to-use and high sensitivity method for constructing a sequencing library based on a single-stranded DNA molecule, which is suitable to trace sample, and the application thereof.

It should be explained that the present invention is based on the following works from the inventors:

Use single-stranded molecule to construct the library, fulfill complementary condition and extension reaction utilizing DNA 3'-terminus Poly(C)$_n$ and extension primer containing Poly(G)$_m$;

Minimize the times of purification through centrifugal column, only purify before amplifying and purify through affinity combination of magnetic bead and biotin to minimize the loss of sample dramatically;

Ligate adapter to one terminus by PCR reaction, amplify the library sample during the time of adding index tab, and form the sequencing library using the amplification product.

Thus according to one of the aspects of the present invention, it is provided that a kind of method for constructing a sequencing library based on a single-stranded DNA molecule. According to the embodiment of the present invention, the method comprising: (1) forming a poly(C)n tail at a 3'-terminus of the single-stranded DNA molecule, to obtain a single-stranded DNA molecule with the poly(C)n tail with n representing a number of base C, and n being an integer ranging from 5 to 30; (2) obtaining a double-stranded DNA molecule by using an extension primer based on the single-stranded DNA molecule with the poly(C)n tail, with the extension primer comprising a H(G)m unit at a 3'-terminus thereof, H being base A, base T or base C, m being a number of base G, and m being an integer ranging from 5 to 15; and (3) ligating an adapter to one terminus of the double-stranded DNA molecule remote from the H(G)m unit, and amplifying the resulting ligation product to obtain an amplification product forming the sequencing library.

Using the method for constructing a sequencing library based on a single-stranded DNA molecule according to the embodiment of the present invention can construct the sequencing library of single-stranded DNA effectively, especially that of trace sample. DNA 3'-terminus Poly(C)$_n$ and extension primer containing Poly(G)$_m$ are utilized to fulfill complementary pairing and extension reaction of single-stranded DNA, which can avoid extension primer from complementary pairing with genome DNA but not its 3'-terminus to reduce deviation and simultaneously remain the specificity of DNA, and additionally can be applied to research on cell genome methylation information. Moreover single step of purification or no purification can dramatically reduce sample damage and a huge amount of gene information loss for multiple steps of purification thus to decrease the beginning amount of DNA for library construction. As a result, the method provided by the present invention can be efficiently and sensitively applied in high throughput sequencing technology to gain gene sequence information effectively based on sequencing data analysis.

According to one of the aspects of the present invention, an apparatus for constructing a sequencing library based on a single-stranded DNA molecule is also provided. According to embodiment of the present invention, the apparatus comprises the following parts: a tail-ligating unit to form a poly(C)n tail at a 3'-terminus of the single-stranded DNA molecule, to obtain a single-stranded DNA molecule with the poly(C)n tail with n representing a number of base C, and n being an integer ranging from 5 to 30; an extension unit connected to the tail-ligating unit to obtain a double-stranded DNA molecule by using an extension primer based on the single-stranded DNA molecule with the poly(C)n tail, with the extension primer comprising a H(G)m unit at a 3'-terminus thereof, H being base A, base T or base C, m being a number of base G, and m being an integer ranging from 5 to 15; an adapter-ligating unit connected to the extension unit to ligate an adapter to one terminus of the double-stranded DNA molecule remote from the H(G)m unit; and an amplification unit connected to the adapter-ligating unit to amplify the resulting ligation product to obtain an amplification product forming the sequencing library.

Using the apparatus for constructing sequencing library based on single-stranded DNA molecule according to the present invention's embodiment can construct sequencing library of trace single-stranded DNA sample, maintain the specificity of single-stranded DNA strand, maintain integrity of gene information for less sample loss, and be used in construction of genome methylation DNA library.

According to further aspect of the present invention, a method for determining a sequence information of a single-stranded DNA molecule is provided. According to the embodiment of the present invention, the method comprises the following steps: constructing a sequencing library based on the single-stranded DNA molecule by the said methods; sequencing the sequencing library to obtain a sequencing result; and determining the sequence information of the single-stranded DNA molecule based on the sequencing result.

Using the method for determining a sequence information of a single-stranded DNA molecule provided by the embodiment of the present invention can sensitively, precisely and efficiently determine the sequencing information of trace single-stranded DNA sample. It can be applied to cell genome methylation DNA molecular to test the methylation of sample genome or specific section of genome.

According to the other aspect of the present invention, a system for determining a sequence information of a single-stranded DNA molecule is provided. According to embodiment of the present invention the system comprises: a sequencing-library-constructing apparatus, being an apparatus for constructing sequencing library of sample gene based on the said method; a sequencing apparatus connected to the sequencing-library-constructing apparatus to sequence the sequencing library to obtain a sequencing result; and an analysis apparatus to analyze the sequencing result to determine the sequence information of the single-stranded DNA molecule.

Using the system for determining a sequence information of a single-stranded DNA molecule provided by the embodiment of the present invention can sensitively, precisely and efficiently determine the sequencing information of trace single-stranded DNA sample. It can be applied to analyze genome methylation DNA molecular to test the methylation of sample genome or specific section of genome.

According to still the other aspect of the present invention, a method for determining a sequence data of a RNA sample is provided. According to the embodiment of the present invention, the method comprises the following steps: subjecting a RNA sample to reverse transcription to obtain a single-stranded DNA molecule; constructing a sequencing library based on the single-stranded DNA molecule by a method according to the present disclosure; sequencing the sequencing library to obtain a sequencing result; and determining the sequence information of the RNA sample based on the sequencing result.

Using the method for determining a sequence data of a RNA sample provided by the embodiment of the present invention can sensitively, precisely and efficiently determine the sequencing information of trace single-stranded RNA sample to test genome of sample.

According to one aspect of the present invention, a method for determining a sequence data of a target region in a chromatin is provided. According to the embodiment of the present invention, the method comprises the following steps: subjecting a chromatin to random fragmentation to obtain a chromatin sample with a length ranging from 200 bp to 500 bp; subjecting the chromatin sample to a Chromatin Immunoprecipitation to obtain a double-stranded DNA sample by using an antibody specific to the target region; subjecting the double-stranded DNA sample to a denaturation treatment to obtain a single-stranded DNA molecule; constructing a sequencing library based on the single-stranded DNA molecule by a method according to the present disclosure; sequencing the sequencing library to obtain a sequencing result; and determining the sequence data of the target region in the chromatin based on the sequencing result.

Using the method for determining a sequence data of a target region in a chromatin provided by the embodiment of the present invention can sensitively, precisely and efficiently determine the sequencing information of trace target region in a chromatin sample to test genome target region of chromatin sample.

According to the other aspect of the present invention, a method for determining a methylation information in a genome is provided. According to the embodiment of the present invention, the method comprises the following steps: subjecting at least a part of the genome to a bisulfite treatment to transform an unmethylated cytosine into a uracil and obtain a transformed genome sample; subjecting transformed genome sample to random fragmentation to obtain a double-stranded DNA sample with a length ranging from 200 bp to 500 bp; subjecting the double-stranded DNA sample to a denaturation treatment to obtain a single-stranded DNA molecule; constructing a sequencing library based on the single-stranded DNA molecule by the said method; sequencing the sequencing library to obtain a sequencing result; and determining the sequence data of the target region in the chromatin based on the sequencing result.

Using the method for determining methylation information in a genome provided by the embodiment of the present invention can precisely determine the methylation information of sample genome or specific section of genome to test methylation of sample genome or specific section of genome.

More aspects and advantages will be described below, at least a part thereof will be clear in the following description accompanying the figures as attached, and/or be obvious for a person normally skilled in the art from embodiments described hereinafter.

BRIEF DESCRIPTION OF THE FIGURES

The aforementioned features and advantages of the invention as well as additional features and advantages thereof will be more clearly understood hereafter as a result of a detailed description of the following embodiments when taken conjunction with the drawings, wherein:

FIG. 7 shows diagram of the apparatus for constructing sequencing library based on single-stranded DNA according to one embodiment of the invention, Wherein.

DETAILED DESCRIPTION OF THE EMBODIMENTS

Figure 1:
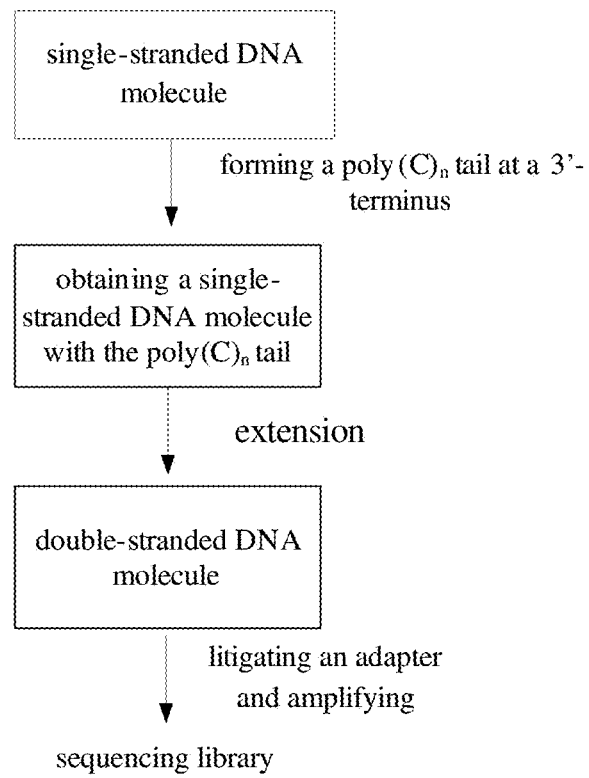
FIG. 1 shows flow chart of the method for constructing a sequencing library based on a single-stranded DNA molecule according to one embodiment of the invention.

The aforementioned features and advantages of the invention as well as additional features and advantages thereof will be more clearly understood hereafter as a result of a detailed description of the following embodiments when taken conjunction with the drawings.

The embodiments described herein with reference to drawings are explanatory, illustrative, and used to generally understand the present invention. The embodiments shall not be construed to limit the scope of the present invention. The same or similar elements and the elements having same or similar functions are denoted by like reference numerals throughout the descriptions.

Method for Constructing Sequencing Library Based on Single-Stranded DNA Molecule According to one aspect of the present invention, method for constructing a sequencing library based on a single-stranded DNA molecule is provided. (Ref. FIG. 1) According to the embodiment of the present invention, the method comprises the following steps:

Firstly forming a poly(C)n tail at a 3'-terminus of the single-stranded DNA molecule, to obtain a single-stranded DNA molecule with the poly(C)n tail with n representing a number of base C, and n being an integer ranging from 5 to 30.

According to the embodiment of the present invention, the said single-stranded DNA molecular may be obtained from RNA reverse transcription. According to another embodiment of the present invention, the said single-stranded DNA molecular may be cDNA molecular obtained from RNA reverse transcription. According to the embodiment of the present invention, the said single-stranded DNA molecular may be obtained by denaturation of a double-stranded DNA sample. According to another embodiment of the present invention, the said single-stranded DNA molecular may be obtained by a thermal denaturation of the double-stranded DNA sample. It has been found surprisingly that specificity of single-stranded DNA may be maintained by constructing sequence library using single-stranded DNA. According to one embodiment of the present invention the double-stranded DNA may be obtained by Chromatin Immunoprecipitation. According to one embodiment of the present invention the double-stranded DNA may be obtained by subjecting a DNA sample to a random fragmentation. According to embodiment of the present invention, the resulting random fragmentation product can be screened after the random fragmentation. According to embodiment of the present invention, method of random fragmentation on DNA sample may be physical method, thus chemical component of sample DNA will not be destroyed, which will improve the accuracy and efficiency of the following sequencing. Examples of physical method for random fragmentation include, but are not limited to, high-pressure-gas atomization treatment, ultrasonic treatment and hydraulic shear force. According to embodiment of the present invention, method of the random fragmentation is ultrasonic treatment. According to embodiment of the present invention, the length of the single-stranded DNA molecule may be 200~500 nt. According to embodiment of the present invention, if method of the random fragmentation is mechanical fragmentation, there should be a step of end-repairing the resulting random fragmentation product after the random fragmentation. For example, reaction system of end-repairing is consisting of 32.6 μl DNA sample, 4 μl 10× T4 ligase buffer solution (NEB, B0202S), 1.6 μl 10 mM dNTP mix (NEB, N0447S), 0.8 μl T4 PNK (NEB, M0201S), 0.8 μl T4 DNA polymerase (NEB, M0203S) and 0.16 μl Klenow fragment (NEB, M0210S). Blending the system and reacting at 20° C. for 30 minutes. Purifying the reaction product by MinElute PCR purification kit (Qiagen, 28006) to gain end-repairing double-stranded DNA fragment. According to specific embodiment of the present invention, the single-stranded DNA molecular weight ≥25 pg. Thus the beginning weight for constructing sequencing library according to the method of the present invention is obviously less than that of other second generation sequencing technology, which can be applied to sequencing library construction for trace sample, especially for scarce sample or sample from clinical patients. According to specific embodiment of the present invention, the single-stranded DNA molecular weight is 25 pg~10 ng. Thus sequencing library construction is high efficiency and accuracy.

Figure 2:
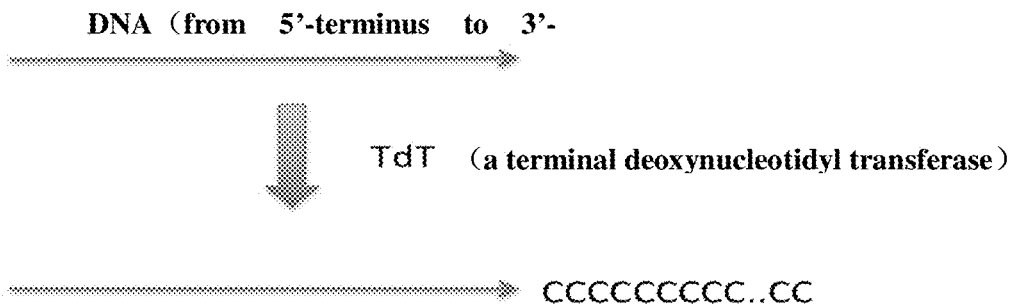
FIG. 2 shows diagram of tail ligation reaction according to one embodiment of the invention.

According to embodiment of the present invention, n of poly(C)$_n$ tail may be an integer ranging from 15 to 25. According to specific embodiment of the present invention, n may be 20. Thus it can combine with extension primer well. According to specific embodiment of the present invention, poly(C)$_n$ tail may be formed by terminal transferase. (Ref. FIG. 2) Single-stranded DNA 3'-terminus can connect with multiple poly-cytosine-deoxynucleotidyl Poly (C)$_n$. The reaction process is: mix 28 μl DNA solution, 1 μl 10×EX buffer solution (Takara, supplied with RR006A) and 1 μl 1 mM dCTP (NEB, N0446S) in advance. Make DNA degenerate under high temperature to obtain single-stranded DNA molecular. Then add 1 μl terminal transferase (TdT; NEB, M0315S) and react at 37° C. for 35 min. After reaction, heat to 75° C. for 20 min to make TdT inactivate and obtain single-stranded DNA molecular whose 3'-terminus connect with oligomeric Poly(C)$_n$.

Than obtaining a double-stranded DNA molecule by using an extension primer based on the single-stranded DNA molecule with the poly(C)n tail, with the extension primer comprising a H(G)m unit at a 3'-terminus thereof, H being base A, base T or base C, m being a number of base G, and m being an integer ranging from 5 to 15. Thus extension primer can annealing pairing on the proper position of Poly(C)$_n$ tail. According to embodiment of the present invention, m of H(G)$_m$ unit may be 9. Therefor the starting position of annealing pairing between H(G)$_m$ unit and oligomeric Poly(C)$_n$ is the most suitable.

Figure 3:
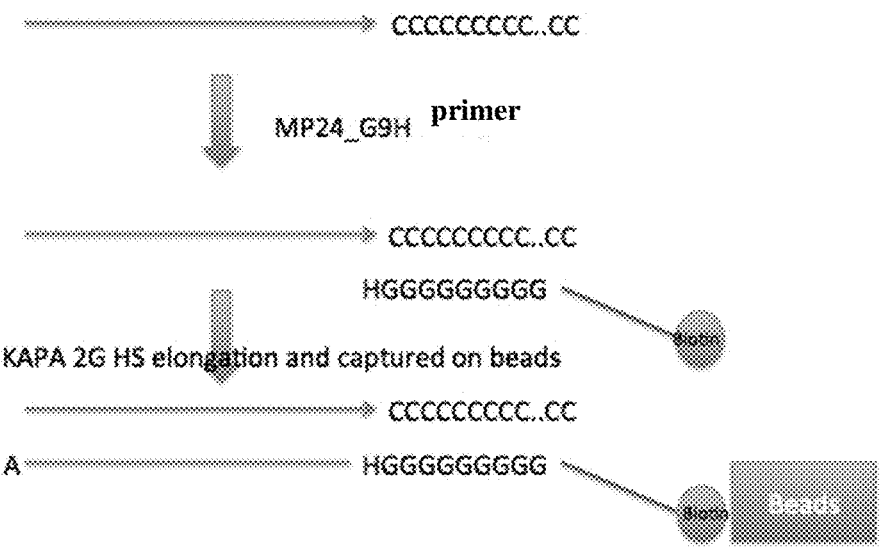
FIG. 3 shows diagram of extension reaction according to one embodiment of the invention.

According to specific embodiment of the present invention, the extension primer has a sequence of SEQ ID NO:1. The specific extension procedure is shown as FIG. 3. Therefor extension primer is easy to pair with poly(C)$_n$ tail and efficiency of extension reaction is high. Wherein specific sequencing of SEQ ID NO: 1 is:

```
                                           (SEQ ID NO: 1)
GTGACTGGAGTTCAGACGTGTGCTGGGGGGGGGH.
```

According to embodiment of the present invention, KAPA 2G Robust HS may be used to extend single-stranded DNA molecular to obtain the double-stranded DNA molecular. For example, reaction system of extension is: single-stranded DNA molecular, whose 3'-terminus connect with oligomeric Poly(C)$_n$, obtained in the former step is mixed with 6.2 µl water, 0.8 µl KAPA 2G Robust HS (KAPA, KK5515), 12 µl 5×KAPA buffer solution A (KAPA, KK5515), 4.8 µl 2.5 mM dNTP (Takara, RR006A) and 6 µl 2 µM extension primer. According to specific embodiment of the present invention, the procedure of extension reaction is: (1) 95° C. 3 min; (2) 47° C. 1 min, 68° C. 2 min, 16 cycles; (3) 72° C. 10 min After the reaction, add exonuclease I (Exo I) and react at 37° C. for 1 hour to digest redundant extension primer and obtain the extension product. Wherein it should be explained that extension strand terminus obtained from extension reaction, that is 3'-terminus of extension strand, is base A, thus connect with semi-adapter having 5'-head of base T.

According to embodiment of the present invention, the extension primer may have selection marker, wherein the selection marker form at the 5'-terminus of extension primer. Thus the extended double-stranded DNA is highly efficiently selected and purified by the selection marker to obtain the aim gene. According to specific embodiment of the present invention, the selection marker is a biotin. Therefor use the method of connecting the DNA fragment with biotin with magnetic bead to purify the extension double-stranded DNA product to decrease the loss of DNA dramatically during purification. According to specific embodiment of the present invention, the procedure of connection between biotin and magnetic bead is shown as the following: washing magnetic streptavidin C1 magnetic bead (Invitrogen, 650.01) in advance with 1× Binding & Wash (B&W) buffer solution (10 mM Tris-HCl pH 8.0, 0.5 mM EDTA, 1 M NaCl), then mix with the extension product and incubation together in temperature control blending instrument with condition of 23° C., 1400 rpm oscillation (oscillation frequency: oscillate for 10 s, then stop 10 s) for 30 min After reaction, wash magnetic bead combined with DNA by 100 µl 1×B&W buffer solution for one time and 150 µl EBT buffer solution (10 mM Tris-HCl pH 8.0, 0.02% Triton X-100) for three times, resuspend by 8.4 µl elution buffer solution (EB; 10 mM Tris-HCl pH 8.0) in the end, which will be used in the ligation reaction.

Figure 4:
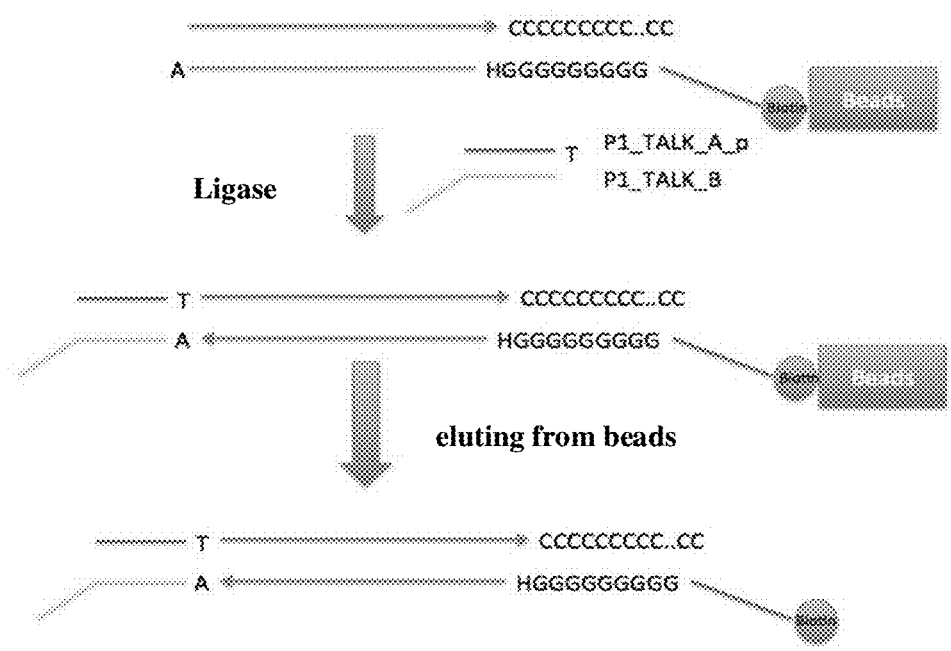
FIG. 4 shows diagram of tail ligation reaction according to one embodiment of the invention.

Finally ligating an adapter to one terminus of the double-stranded DNA molecule remote from the H(G)m unit, and amplifying the resulting ligation product to obtain an amplification product forming the sequencing library. According to embodiment of the present invention, the detailed procedure see FIG. 4, this step further comprises: annealing single-stranded nucleic acids having nucleotide sequences of SEQ ID NOs: 2-3 respectively to form a semi-adapter and ligating the semi-adapter with one terminus of the double-stranded DNA molecule to obtain a double-stranded DNA molecule with the semi-adapter. It should be explained that if bead ligates with one terminus of double-stranded DNA, there will have inhibition. So semi-adapter should ligate with terminus remote from double-stranded DNA bead ligation terminus. Wherein 3'-terminus of semi-adapter SEQ ID NO: 2-3 all has phosphate modification to prevent from self-ligation. Semi-adapter ligation primer's nucleotide sequencing is:

```
                                           (SEQ ID NO: 2)
Adp_A: GACGCTCTTCCGATCT;

(SEQ ID NO: 3)
Adp_B: GATCGGAAGAGCGTCGTGTAGGGAAAGAGTGT
```

According to specific embodiment of the present invention, ligation reaction condition is: put 1 µl Rapid DNA ligase (NEB, M2200L), 10 µl 2× rapid ligation buffer solution, 8.4 µl resuspending magnetic bead combined with extension product and 0.6 µl 10 mM adapter into centrifuge tube and mix totally. Put the centrifuge tube on rotating culture device to avoid magnetic bead settlement. React overnight at 4° C. (about 15 hours) to obtain the double-stranded DNA molecule with adapter. Thus the background of ligation is small and efficiency of ligation is high. According to embodiment of the present invention, purify the resulting ligation product before the amplification. According to specific embodiment of the present invention, purification may be done by using a bead specific to the biotin. According to another specific embodiment of the present invention, the bead may be magnetic bead provided with a streptavidin. Thus method for purifying the extension double-stranded DNA product by magnetic bead combination with DNA fragment with biotin has good purifying effect and decrease DNA loss dramatically during purification. According to embodiment of the present invention, elute purification product using ultra pure distilled water at 72° C., double-stranded DNA molecule with the semi-adapter being in eluent, to obtain a purified double-stranded DNA molecule with the semi-adapter. Thus eluent with double-stranded DNA molecule with the semi-adapter may be used in the following amplification product directly to reduce intermediate steps and avoid DNA loss.

Figure 5:
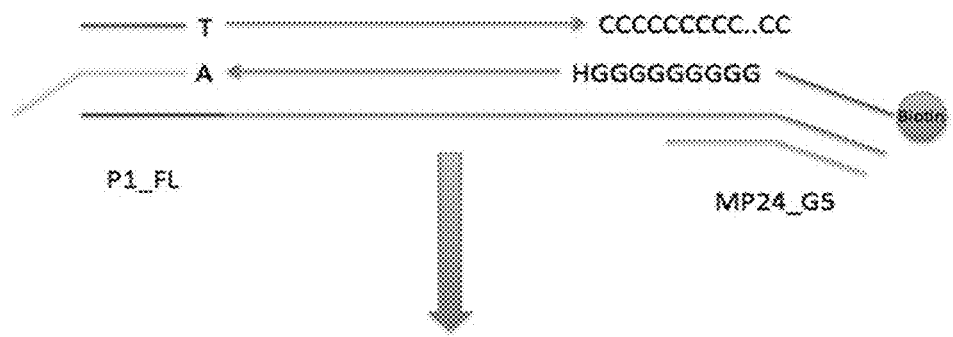
FIG. 5 shows diagram of the first round of PCR amplified reaction according to one embodiment of the invention.
Figure 5:
Figure 6:
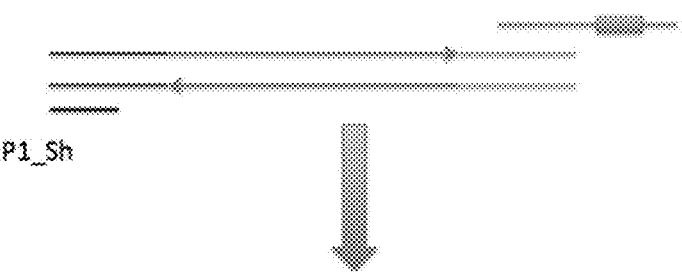
FIG. 6 shows diagram of the second round of PCR amplified reaction to obtain the whole library sample according to one embodiment of the invention.

After obtain the double-stranded DNA molecule with the semi-adapter, amplify the double-stranded DNA molecule with the semi-adapter to obtain amplification product which consist the sequencing library. According to embodiment of the present invention, use two round of PCR. In the first round of PCR (Ref. FIG. 5) use nucleotides of SEQ ID NO: 4-5 as primer to amplify double-stranded DNA molecule with the semi-adapter, which has high amplification efficiency of DNA molecule. In the second round of PCR (Ref. FIG. 6) use nucleotides of SEQ ID NO: 4-5 as primer, which has high amplification efficiency of DNA molecule. Wherein amplification primer has the nucleotides sequencing of the following:

Amplification Primer:
First Round of PCR:

```
MP24_G5:
                                           (SEQ ID NO: 4)
GTGACTGGAGTTCAGACGTGTGCTGGGGG,

P1_FL:
                                           (SEQ ID NO: 5)
AATGATACGGCGACCACCGAGATCTACACTCTTTCCCTACACGACGCTCT

TCCGATCT;
```

Second Round of PCR:

P1_Sh: AATGATACGGCGACCACCGA (SEQ ID NO: 6)

Index Sequence without Index:

CAAGCAGAAGACGGCATACGAGATNNNNNNGTGACTGGAGTTCAGACG (SEQ ID NO: 7)

According to embodiment of the present invention, primer with Index sequence may be used in the amplification unit to amplify the ligation product. Therefor multiple samples can be tested in one time of high-throughput sequencing. For example, add distinguished Index sequence on one terminus of DNA library, which can be used to construct Illumina high-throughput sequencing standard library sample.

The term "indexed-primer" means inserting sequence index into PCR primer sequence. Therefor indexed-primer may be insert into one terminus of aim segment, either 5'-terminus or 3'-terminus, during amplification using Index sequence primer. For example, Ref. FIG. 6, when using index PCR primer as upstream primer, that is to say inserting sequence index on 5'-terminus of aim segment, Index sequence primer is specific to 5'-adapter sequence and downstream primers is specific to 3'-adapter sequence. Connecting DNA molecule by Index sequence primer can characterize sample source of DNA molecule precisely. Therefor using the nucleic acid index can construct sequencing DNA library applied into many kinds of DNA molecule. So through mixing DNA libraries from different source of samples, multiple sequencing may be done in one time and DNA sequence may be classified based on Index sequence to obtain sequence information of many kinds of DNA molecule. Multiple DNA molecule sequencing may be achieved by high throughput sequencing technology, such as Solexa sequencing technology, to improve efficiency and throughput of DNA molecule sequencing. According to embodiment of the present invention, using PCR primer constituted by anyone of SEQ ID NO: 8~19 nucleotide shown table 1 as index PCR primer, which may improve the sequencing accuracy more. In the description, nucleic acid index is named as IndexN respectively, wherein N may be an integer between 1 and 12. The sequence is shown as the following table 1:

TABLE 1 sequence of nucleic acid index sequence primer Index 1-12

| Name of primer | sequence |
|---|---|
| Index01 | CAAGCAGAAGACGGCATACGAGATCGTGATGTGACTGG AGTTCAGACG (SEQ ID NO: 8) |
| Index02 | CAAGCAGAAGACGGCATACGAGATACATCGGTGACTGG AGTTCAGACG (SEQ ID NO: 9) |
| Index03 | CAAGCAGAAGACGGCATACGAGATGCCTAAGTGACTGG AGTTCAGACG (SEQ ID NO: 10) |
| Index04 | CAAGCAGAAGACGGCATACGAGATTGGTCAGTGACTGG AGTTCAGACG (SEQ ID NO: 11) |
| Index05 | CAAGCAGAAGACGGCATACGAGATCACTGTGTGACTGG AGTTCAGACG (SEQ ID NO: 12) |

TABLE 1-continued sequence of nucleic acid index sequence primer Index 1-12

| Name of primer | sequence |
|---|---|
| Index06 | CAAGCAGAAGACGGCATACGAGATATTGGCGTGACTGG AGTTCAGACG (SEQ ID NO: 13) |
| Index07 | CAAGCAGAAGACGGCATACGAGATGATCTGGTGACTGG AGTTCAGACG (SEQ ID NO: 14) |
| Index08 | CAAGCAGAAGACGGCATACGAGATTCAAGTGTGACTGG AGTTCAGACG (SEQ ID NO: 15) |
| Index09 | CAAGCAGAAGACGGCATACGAGATCTGATCGTGACTGG AGTTCAGACG (SEQ ID NO: 16) |
| Index10 | CAAGCAGAAGACGGCATACGAGATAAGCTAGTGACTGG AGTTCAGACG (SEQ ID NO: 17) |
| Index 11 | CAAGCAGAAGACGGCATACGAGATGTAGCCGTGACTGG AGTTCAGACG (SEQ ID NO: 18) |
| Index12 | CAAGCAGAAGACGGCATACGAGATTACAAGGTGACTGG AGTTCAGACG (SEQ ID NO: 19) |

As a result, the method provided by the present invention can easily construct gene sequencing library of multiple samples simultaneously and be applied on high-throughput sequencing plat effectively. After data analyzing on sequencing result, based on sequence information of index, sequence information of gene sequencing library from multiple samples may be distinguished accurately. Therefor the method can use high-throughput sequencing plat adequately, save time and reduce cost.

Figure 7A:
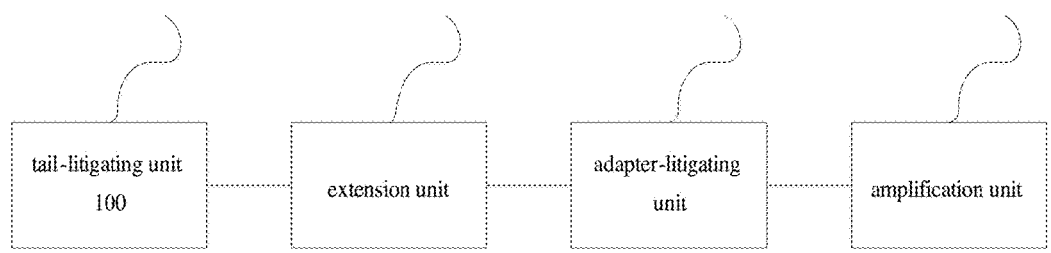
FIG. 7A shows diagram of the apparatus for constructing sequencing library based on single-stranded DNA sample.

Apparatus for Constructing a Sequencing Library Based on Single-Stranded DNA Molecule According to another aspect of the present invention, it is also provided that a kind of apparatus for constructing a sequencing library based on a single-stranded DNA molecule. Ref. FIG. 7A. According to embodiment of the present invention, the apparatus may comprise: tail-ligating unit 100, extension unit 200, adapter-ligating unit 300 and amplification unit 400.

Tail-ligating unit 100, it is used to form a poly(C)$_n$ tail at a 3'-terminus of the single-stranded DNA molecule to obtain single-stranded DNA molecule with the poly(C)$_n$ tail with n representing a number of base C, and n being an integer ranging from 5 to 30. According to embodiment of the present invention, the tail-ligating unit may have terminal deoxynucleotidyl transferase. Thus add the poly(C)$_n$ tail to 3'-terminus of the single-stranded DNA molecule efficiently.

Extension unit 200, connected to the tail-ligating unit 100, it is used to obtain a double-stranded DNA molecule by using an extension primer based on the single-stranded DNA molecule with the poly(C)$_n$ tail, with the extension primer comprising a H(G)$_m$ unit at a 3'-terminus thereof, H being base A, base T or base C, m being a number of base G, and m being an integer ranging from 5 to 15. According to embodiment of the present invention, the extension unit may set with KAPA 2G Robust HS to obtain the double-stranded DNA molecule. According to embodiment of the present invention, the extension primer may be constituted by nucleotide of SEQ ID NO: 1. According to embodiment of the present invention, the extension primer set in the extension unit may have selection marker formed at a 5'-terminus of the extension primer. According to specific embodiment of the present invention, the selection marker is a biotin.

Adapter-ligating unit 300, connected to the extension unit 200, it is used to ligate an adapter to one terminus of the double-stranded DNA molecule remote from the $H(G)_m$ unit. According to embodiment of the present invention, the adapter-ligating unit 300 may further comprises: semi-adapter-forming module to anneal single-stranded nucleic acids having nucleotide sequences of SEQ ID NOs: 2-3 respectively to form a semi-adapter; and ligating module to ligate the semi-adapter with one terminus of the double-stranded DNA molecule to obtain a double-stranded DNA molecule with the semi-adapter. Thus ligate semi-adapter with terminus remote from $H(G)_m$ unit on double-stranded DNA molecule to avoid forming too long adapter sequence to ligate efficiently.

Amplification unit 400, connected to the adapter-ligating unit 300, it is used to amplify the resulting ligation product to obtain an amplification product forming the sequencing library. According to embodiment of the present invention, use two rounds of PCR. In the first round of PCR use nucleotides of SEQ ID NO: 4-5 as primer to amplify double-stranded DNA molecule with the semi-adapter, which has high amplification efficiency of DNA molecule. In the second round of PCR, the amplification unit includes primer containing index sequence to amplify the resulting ligation product. Therefor multiple samples can be tested in one time of high-throughput sequencing. For example, add distinguished Index sequence on one terminus of DNA library, which can be used to construct Illumina high-throughput sequencing standard library sample. According to embodiment of the present invention, using PCR primer constituted by any one of SEQ ID NO: 8~19 nucleotides is shown table 1 as index PCR primer.

As a result, the method provided by the present invention can easily construct gene sequencing library of multiple samples simultaneously and be applied on high-throughput sequencing plat effectively. After data analyzing on sequencing result, based on sequence information of index, sequence information of gene sequencing library from multiple samples may be distinguished accurately. Therefor the method can use high-throughput sequencing plat adequately, save time and reduce cost.

It should be understood by the person skilled in the art that any apparatus suitable to operate the above operation may be used as the component(s) of the above units. And the term "connected" should be understood broadly comprising connected directly or connected indirectly via intermediate, and the person skilled in the art may understand the detailed meaning depending the desired purpose.

Using the apparatus for constructing a sequencing library based on a single-stranded DNA molecule according to embodiments of present disclosure, trace amount of single-stranded DNA molecule may be used to construct a sequencing library with maintaining the specificity of the DNA strand, losing less amount of samples, maintaining the complete gene information, then a whole genomic methylation DNA sequencing library of a cell may be constructed.

Figure 7B:
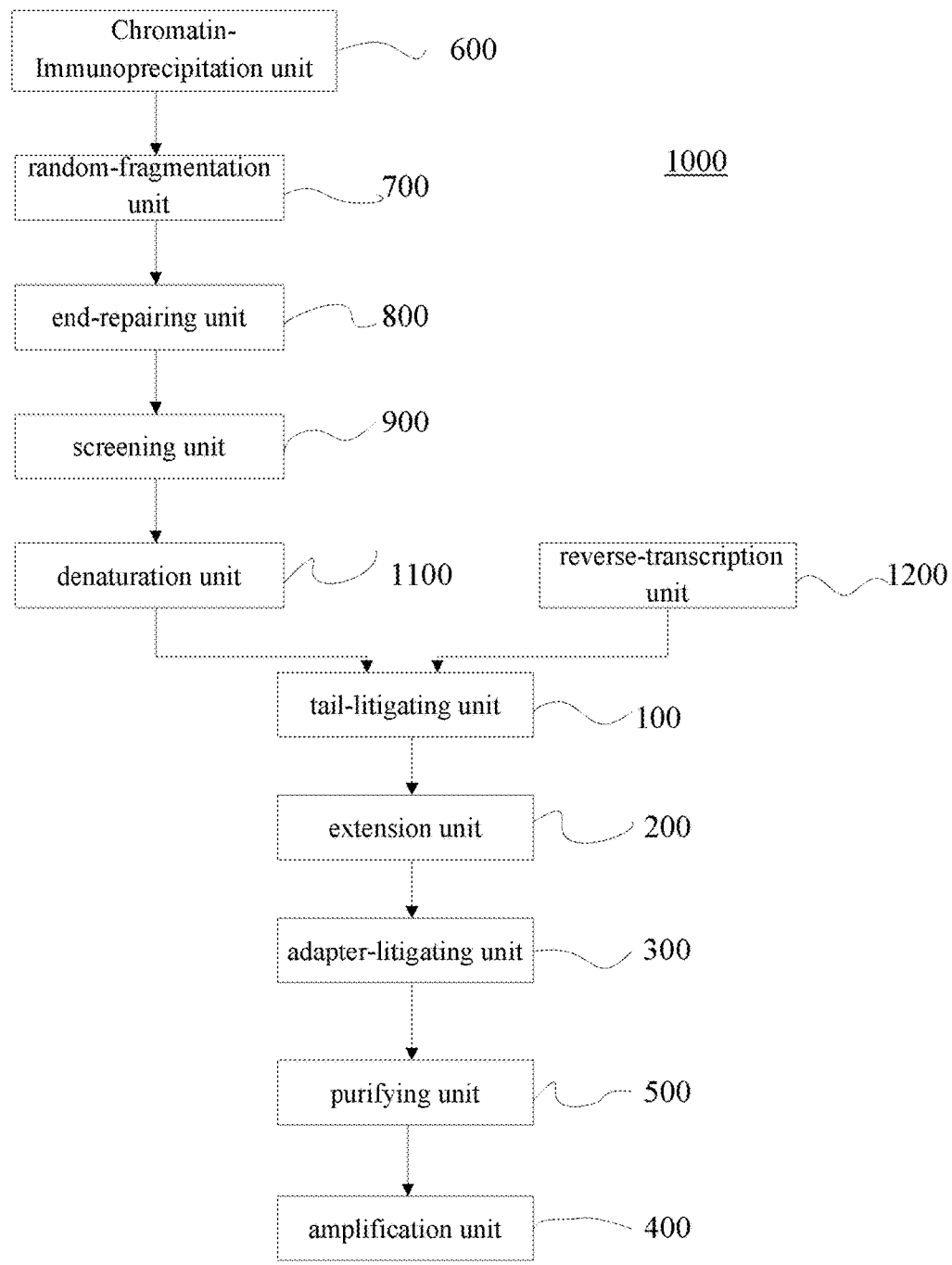
FIG. 7B shows diagram of the apparatus for constructing sequencing library based on RNA or chromatin sample.

According to embodiments of present disclosure, the apparatus for constructing a sequencing library based on a single-stranded DNA molecule may comprise at least one of followings: a reverse-transcription unit, a denaturation unit, a random-fragmentation unit, a screening unit, an end-repairing unit, a Chromatin-Immunoprecipitation unit and a purifying unit. Then the person skilled in the art may choose the unit(s) needed depending on the type of the desired sample to construct the sequencing library. Referring to FIG. 7B, the detailed process may comprises:

Firstly, a series of units to treat the sample obtain single-stranded DNA used to construct sequencing library. If the sample is RNA, a reverse-transcription unit 1200 may be used to subject a reverse transcription to RNA to obtain the single-stranded DNA molecule. If the sample is a cell, the cell should be lysed to release chromatin and DNA may be extracted from the chromatin, then a Chromatin-Immunoprecipitation unit may be used to obtain the double-stranded DNA sample by a Chromatin Immunoprecipitation. A random-fragmentation unit 700 may be connected to the Chromatin-Immunoprecipitation unit 600, if the sample is a genomic DNA or long-stranded DNA, to subject a double-stranded DNA obtained in the Chromatin-Immunoprecipitation unit to random fragmentation to obtain the double-stranded DNA molecule. According to embodiments of present disclosure, the random-fragmentation unit 700 may carry out an ultrasonic random-fragmentation.

Secondly, an end-repairing unit 800 may be connected to the random-fragmentation unit to end-repair the resulting random fragmentation product after the random fragmentation. Then a screening unit 900 may be used to screen the resulting random fragmentation product after the random fragmentation. For example, a screening unit 900 may be connected to the end-repairing unit 800 used to screen the resulting random fragmentation product after the random fragmentation by using a probe specific to the target fragment to obtain target fragments.

Finally, a denaturation unit 1100 may be connected to the screening unit 900 to subject a double-stranded DNA sample to denaturation to obtain the single-stranded DNA molecule. According to embodiments of present disclosure, the denaturation unit 1100 may carry out the denaturation on the double-stranded DNA sample by thermal denaturation and obtain the single-stranded DNA with high efficiency and less loss of DNA molecule.

According to embodiments of present disclosure, a tail-ligating unit 100 may be connected to the denaturation unit 1100 and/or the reverse-transcription unit 1200 to form a poly$(C)_n$ tail at a 3'-terminus of the single-stranded DNA molecule obtained in the denaturation unit 1100 and/or the reverse-transcription unit 1200, to obtain a single-stranded DNA molecule with the poly$(C)_n$ tail with n representing a number of base C, and n being an integer ranging from 5 to 30. According to embodiments of present disclosure, terminal transferase may be provided in the tail-ligating unit 100 to obtain a single-stranded DNA molecule with the poly$(C)_n$ tail with high efficiency.

According to embodiments of present disclosure, KAPA 2G Robust HS may be provided in the extension unit 200, to obtain the double-stranded molecular based on the single-stranded DNA molecule with the poly$(C)_n$ tail. Then DNA may be extended with high efficiency and high accuracy. According to embodiments of present disclosure, the extension primer may be comprised of SEQ ID NO: 1, which is easy to match with poly$(C)_n$ tail and promote the extension reaction. According to embodiments of present disclosure, the extension primer provided in the extension unit may comprise a selection marker formed at a 5'-terminus of the extension primer, and in some embodiments the selection marker is a biotin.

According to embodiments of present disclosure, an adapter-ligating unit 300 may be connected to the extension unit 200 to ligate an adapter to one terminus of the double-stranded DNA molecule remote from the $H(G)_m$ unit. According to embodiments of present disclosure, the adapter-ligating unit may further comprise: a semi-adapter-forming module to anneal single-stranded nucleic acids having nucleotide sequences of SEQ ID NOs: 2-3 respectively to form a semi-adapter; a ligating module to ligate the semi-adapter with one terminus of the double-stranded DNA molecule to obtain a double-stranded DNA molecule with the semi-adapter; and an amplifying module to amplify the double-stranded DNA molecule with the semi-adapter by using nucleotides of SEQ ID NOs: 4-7 as primers. According to embodiments of present disclosure, the ligating module is provided with a Rapid DNA ligase to ligate the semi-adapter with one terminus of the double-stranded DNA molecule. According to embodiments of present disclosure, in the amplifying module, amplifying the resulting ligation product may be performed by using a primer comprising an Index sequence. According to embodiments of present disclosure, the primer comprising an Index sequence is one selected from a set of indexed-primer consisting of SEQ ID NO: 8-19. Then several samples may be sequenced in one time lowering the sequencing cost and improving sequencing efficiency.

According to embodiments of present disclosure, a purifying unit 500 connect to the adapter-ligating unit 300 may be included to purify the resulting ligation product by using a bead specific to the biotin before the amplification. The apparatus according to the present disclosure, wherein the bead is magnetic bead provided with a streptavidin. According to embodiments of present disclosure, an elution unit may be further included to elute a purification product using a water at 72° C. to obtain a purified double-stranded DNA molecule with the adapter. Then the elute containing the double-stranded DNA molecule with semi-adapter may be added to the amplification unit 400 to be amplified eliminating some operation steps avoiding the loss of DNA.

Method and System to Determine Sequence Information of Single-Stranded DNA Molecule In one aspect of present disclosure, a method for determining a sequence information of a single-stranded DNA molecule is provided. According to embodiments of present disclosure, the method comprises: constructing a sequencing library based on the single-stranded DNA molecule by a method described above; sequencing the sequencing library to obtain a sequencing result; and determining the sequence information of the single-stranded DNA molecule based on the sequencing result. According to embodiments of present disclosure, the Next-Generation-Sequencing method may be used for example SOLEXA, SOLID and 454 sequencing platform. And the person skilled in the art may acknowledge that some newly developed method may be also used for example single-molecule sequencing method such as True Single Molecule DNA sequencing method of Helicos, the single molecule, real-time (SMRT™) method of Pacific Biosciences and Nanopore sequencing method of Oxford Nanopore Technologies may be used (Rusk, Nicole (2009 Apr. 1). Cheap Third-Generation Sequencing. *Nature Methods* 6 (4): 244-245 incorporated herein by reference). Using the method for determining a sequence information of a single-stranded DNA molecule provided by the embodiment of the present invention can sensitively, precisely and efficiently determine the sequencing information of trace single-stranded DNA sample. It can be applied to cell genome methylation DNA molecular to test the methylation of sample genome or specific section of genome.

Figure 8:
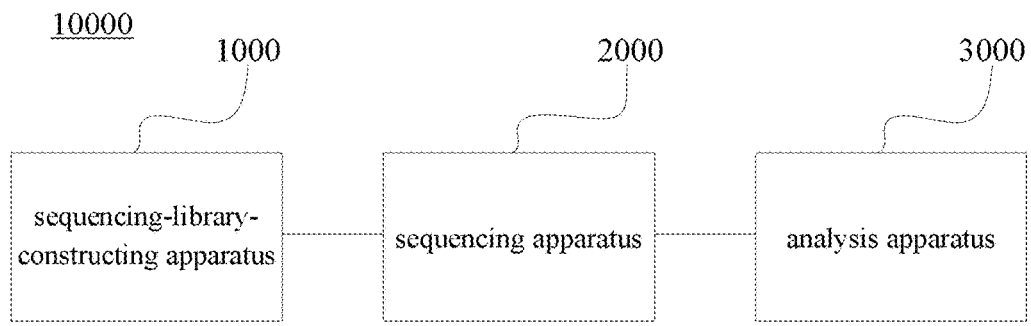
FIG. 8 shows diagram of the system for determining sequencing information of single-stranded DNA according to one embodiment of the invention.

In another aspect of present disclosure, a system for determining a sequence information of a single-stranded DNA molecule is provided. And according to embodiments of present disclosure, the system comprises, referring to FIG. 8, a sequencing-library-constructing apparatus 100 being an apparatus for constructing a sequencing library based on a single-stranded DNA molecule described above; a sequencing apparatus 2000 connected to the sequencing-library-constructing apparatus 1000 to sequence the sequencing library to obtain a sequencing result; and an analysis apparatus 3000 to analyze the sequencing result to determine the sequence information of the single-stranded DNA molecule.

Using the system for determining a sequence information of a single-stranded DNA molecule provided by the embodiment of the present invention can sensitively, precisely and efficiently determine the sequencing information of trace single-stranded DNA sample. It can be applied to analyze genome methylation DNA molecular to test the methylation of sample genome or specific section of genome.

Figure 9:
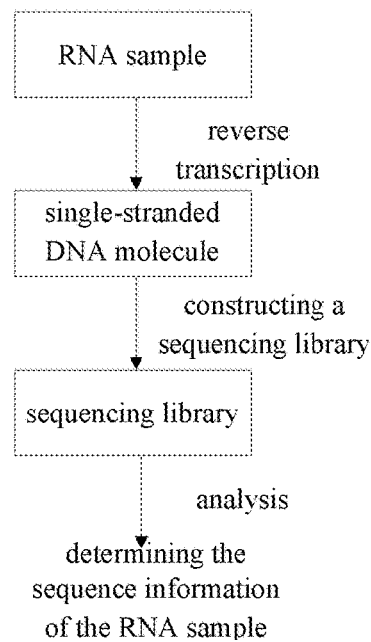
FIG. 9 shows diagram of the method for determining sequencing data of RNA sample according to one embodiment of the invention.

Method for Determining Sequence Data of RNA, Chromatin and Methylation Information According to still the other aspect of the present invention, a method for determining a sequence data of a RNA sample is provided. According to the embodiment of the present invention, referring to FIG. 9, the method comprises the following steps: subjecting a RNA sample to reverse transcription to obtain a single-stranded DNA molecule; constructing a sequencing library based on the single-stranded DNA molecule by a method according to the present disclosure; sequencing the sequencing library to obtain a sequencing result; and determining the sequence information of the RNA sample based on the sequencing result.

Using the method for determining a sequence data of a RNA sample provided by the embodiment of the present invention can sensitively, precisely and efficiently determine the sequencing information of trace single-stranded RNA sample to test genome of sample.

Figure 10:
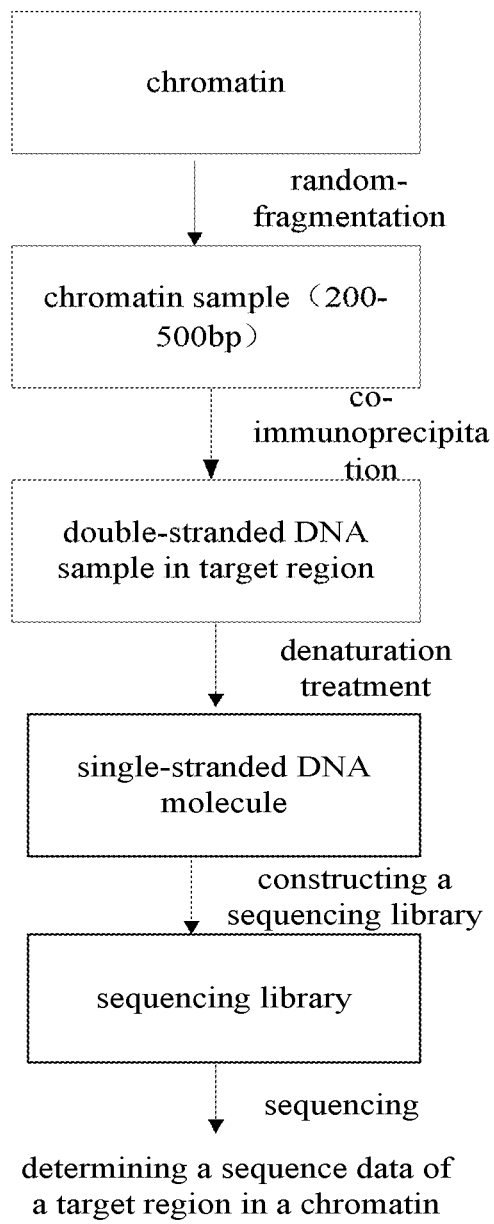
FIG. 10 shows diagram of the method for determining sequence data of a target region in a chromatin according to one embodiment of the invention.

According to one aspect of the present invention, a method for determining a sequence data of a target region in a chromatin is provided. According to the embodiment of the present invention, referring to FIG. 10, the method comprises the following steps: subjecting a chromatin to random fragmentation to obtain a chromatin sample with a length ranging from 200 bp to 500 bp; subjecting the chromatin sample to a Chromatin Immunoprecipitation to obtain a double-stranded DNA sample by using an antibody specific to the target region; subjecting the double-stranded DNA sample to a denaturation treatment to obtain a single-stranded DNA molecule; constructing a sequencing library based on the single-stranded DNA molecule by a method according to the present disclosure; sequencing the sequencing library to obtain a sequencing result; and determining the sequence data of the target region in the chromatin based on the sequencing result.

Using the method for determining a sequence data of a target region in a chromatin provided by the embodiment of the present invention can sensitively, precisely and efficiently determine the sequencing information of trace target region in a chromatin sample to test genome target region of chromatin sample.

Figure 11:
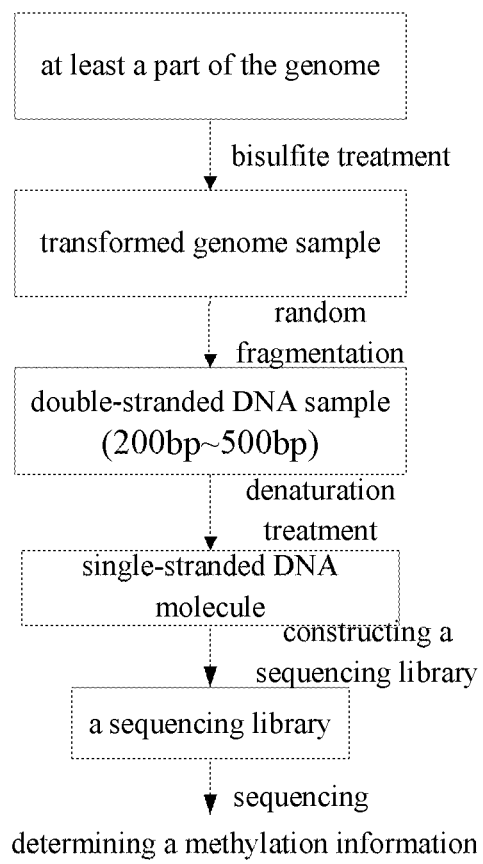
FIG. 11 shows diagram of the method for determining methylation information in a genome according to one embodiment of the invention.

According to the other aspect of the present invention, a method for determining a methylation information in a genome is provided. According to the embodiment of the present invention, referring to FIG. 11, the method comprises the following steps: subjecting at least a part of the genome to a bisulfite treatment to transform an unmethylated cytosine into a uracil and obtain a transformed genome sample; subjecting transformed genome sample to random fragmentation to obtain a double-stranded DNA sample with a length ranging from 200 bp to 500 bp; subjecting the double-stranded DNA sample to a denaturation treatment to obtain a single-stranded DNA molecule; constructing a sequencing library based on the single-stranded DNA molecule by the said method; sequencing the sequencing library to obtain a sequencing result; and determining the sequence data of the target region in the chromatin based on the sequencing result.

Using the method for determining methylation information in a genome provided by the embodiment of the present invention can precisely determine the methylation information of sample genome or specific section of genome to test methylation of sample genome or specific section of genome.

Reference will be made in detail to examples of the present disclosure. It would be appreciated by those skilled in the art that the following examples are explanatory, and cannot be construed to limit the scope of the present disclosure. If the specific technology or conditions are not specified in the examples, a step will be performed in accordance with the techniques or conditions described in the literature in the art or in accordance with the product instructions. If the manufacturers of reagents or instruments are not specified, the reagents or instruments may be commercially available. Descriptions in following brackets respectively illustrate catalog No. of different manufacturers for various reagents or kits. The adaptor and index used for sequencing derive from Multiplexing Sample Preparation Oligonutide Kit of Illumina Company.

EXAMPLES

In the following examples, the following primers were used:

```
Adp_A
GACGCTCTTCCGATCT[Phos]

Adp_B
[Phos]GATCGGAAGAGCGTCGTGTAGGGAAAGAGTGT[Phos]

MP24_G9H
[Btn]GTGACTGGAGTTCAGACGTGTGCTGGGGGGGGGH

MP24_G5
GTGACTGGAGTTCAGACGTGTGCTGGGGG

P1_FL
AATGATACGGCGACCACCGAGATCTACACTCTTTCCCT

ACACGACGCTCTTCCGATCT

P1_Sh
AATGATACGGCGACCACCGA

Index01
CAAGCAGAAGACGGCATACGAGATCGTGATGTGACT

GGAGTTCAGACG

Index02
CAAGCAGAAGACGGCATACGAGATACATCGGTGACT

GGAGTTCAGACG

Index03
CAAGCAGAAGACGGCATACGAGATGCCTAAGTGACT

GGAGTTCAGACG

Index04
CAAGCAGAAGACGGCATACGAGATTGGTCAGTGACT

GGAGTTCAGACG

Index05
CAAGCAGAAGACGGCATACGAGATCACTGTGTGACT

GGAGTTCAGACG

Index06
CAAGCAGAAGACGGCATACGAGATATTGGCGTGACT

GGAGTTCAGACG

Index07
CAAGCAGAAGACGGCATACGAGATGATCTGGTGACT

GGAGTTCAGACG

Index08
CAAGCAGAAGACGGCATACGAGATTCAAGTGTGACT

GGAGTTCAGACG

Index09
CAAGCAGAAGACGGCATACGAGATCTGATCGTGACTG

GAGTTCAGACG

Index10
CAAGCAGAAGACGGCATACGAGATAAGCTAGTGACT

GGAGTTCAGACG

Index11
CAAGCAGAAGACGGCATACGAGATGTAGCCGTGACT

GGAGTTCAGACG

Index12
CAAGCAGAAGACGGCATACGAGATTACAAGGTGACT

GGAGTTCAGACG
```

Example 1 Construction of Sequencing Library

1. Qubit fluorometer (Invitrogen, Q32857) was used to determine the amount of DNA to construct sequencing library, Qubit dsDNA HS assay kit (Invitrogen, Q32854) was used for double-stranded DNA, and Qubit ssDNA HS assay kit (Invitrogen, Q10212) was for single-stranded DNA. The starting amount of the DNA for sequencing library was 25 pg to 10 ng, and the following steps were used.

For trace amount of double-stranded DNA (for example ChIP-Seq DNA) obtained by mechanical random fragmentation (for example ultrasonic fragmentation), the 5'-terminus and 3'-terminus was firstly end-repaired in a reaction system comprising:

32.6 μl DNA sample;
4 μl 10× T4 ligase buffer (NEB, B0202S);
1.6 μl 10 mM dNTP mix (NEB, N0447S);
0.8 μl T4 PNK (NEB, M0201S);
0.8 μl T4 DNA polymerase (NEB, M0203S); and
0.16 μl Klenow fragment (NEB, M0210S).

The reaction was carried out at 20° C. for 30 min. And the reaction product was purified using MinElute PCR purification kit (Qiagen, 28006).

The reaction system and conditions of the DNA end-repairing was summarized in the following table.

| Reagent | volume(μl) |
| --- | --- |
| DNA + water | 32.6 |
| 10× T4 ligase buffer | 4 |
| 10 mM dNTP mix | 1.6 |

| Reagent | volume(μl) |
| --- | --- |
| T4 PNK | 0.8 |
| T4 DNA polymerase | 0.8 |
| Klenow | 0.16 |
| Total volume | 40 |
| 20° C. for 30 min (in a PCR machine) | |
| Purify DNA using a Minelute column | |
| PB buffer | 240 |
| Elution buffer | 15 (×2) |
| Total volume | 28 μl |

2. Formation of a Tail: Adding Several dCMP (Poly-C)

A terminal deoxynucleotidyl transferase (TdT) was used to adding several (about 20) dCMP (poly-C). The process of the reaction was:

Mixing 28 μl DNA solution, 1 μl 10×EX buffer (Takara, supplied with RR006A), 1 μl 1 mM dCTP (NEB, N0446S), heating DNA for denaturation. And adding 1 μl terminal deoxynucleotidyl transferase (TdT; NEB, M0315S), and reacting at 37° C. for 5 min After the reaction, the reaction system was heated to 75° for 20 min to deactivate TdT.

The reaction system and conditions of the tail formation reaction was summarized in following table.

| reagent | volume (μl) |
| --- | --- |
| DNA (in water or elution buffer) | 28 |
| 10x EX buffer | 1 |
| 1 mM dCTP | 1 |
| 95° C. 1 min (in PCR machine), cooling rapidly on ice for 1 min | |
| TdT Enzyme | 1 |
| 37° C. 35 min | |
| 1 mM dATP (optional) | 1 |
| 37° C. 5 min | |
| 75° C. 20 min | |
| For ever at room temperature | |

3. Strand Extension Reaction: Form a Double-Stranded DNA Based on the Single-Stranded DNA with Poly-C Tail at 3'-Terminus by Extension Reaction Reaction System:

Reaction product of TdT reaction of step 2 with 6.2 μl water;

0.8 μl KAPA 2G Robust HS (KAPA, KK5515);

12 μl 5×KAPA buffer A (KAPA, KK5515);

4.8 μl 2.5 mM dNTP (Takara, RR006A);

6 μl 2 μM extension primer with biotin (biotin-labeled anchor primer).

The extension primer was designed to have 9 consecutive dGMPs (G) and one H (H is A, T or C) to ensure the primer may match the Poly-C at proper site.

The procedure for the extension reaction was:

(1) 95° C. 3 min;

(2) 47° C. 1 min, 68° C. 2 min, 16 cycles;

(3) 72° C. 10 min.

After the reaction, ExoI was added at 37° C. for 1 hour to digest the remaining extension primer.

magnetic streptavidin C1 beads (Invitrogen, 650.01) prewashed with 1× Binding & Wash (B&W) buffer (10 mM Tris-HCl pH 8.0, 0.5 mM EDTA, 1 M NaCl was mixed with the extension reaction product and incubated the mixture at 23° C. with vortexing under 1400 rpm (10 sec on, 10 sec off) 30 min After the reaction, beads attached with DNA were washed with 100 μl 1×B&W buffer for one time, with 150 μl EBT buffer (10 mM Tris-HCl pH 8.0, 0.02% Triton X-100) for three times, and resuspended the product with 8.4 μl washing buffer (EB; 10 mM Tris-HCl, pH 8.0) for the following ligation reaction.

The reaction system and conditions of the strand extension reaction was summarized in following table.

| reagent | volume(μl) |
| --- | --- |
| TdT reaction product | about 30 |
| Mixed with the followings | |
| water | 6.2 |
| 5x KAPA buffer A | 12 |
| 2.5 mM dNTP | 4.8 |
| 2 mM extension primer | 6 |
| KAPA 2G polymerase | 0.8 |
| Mixture system total volume | 29.8 |
| Reaction system total volume | about 60 |
| Run a procedure in a PCR machine: | |
| 95° C. 3 min, (47° C. 1 min, 68° C. 2 min) x16 c, 72° C. 10 min | |
| Digesting the remaining primers | |
| 10x Exo I buffer | 6 |
| Exonuclease I | 2 |
| 37° C. 40~60 min | |
| 4x B&W buffer | 22 |
| Total | ~90 |

The conditions for recovering magnetic beads were summarized in the following table:

| Reagent | volume(μl) |
| --- | --- |
| Streptavidin C1 magnetic bead | 8 |
| Supernatant was removed, and the pellet was washed with 100 μl 1x B&W for 2 or 3 times | |
| Resuspended the pellet with 10 μl 1x B&W buffer | |
| Mixing the followings: | |
| Beads suspension | 10 |
| Extension product after digestion | 90 |
| Vortexing at 1400 rpm(10" on 10" off), 23° C. 15~30 min | |
| washing (1x B&W) | 100 (×1) |
| washing (EBT) | 150 (×3) |
| resuspensionbuffer(EB) | 8.4 |
| For next step (s). | |

4. Ligating an Adapter at Another Terminus

An adapter was formed by annealing Adp_A and Adp_B, both of which were primers modified with phosphate group at 3' terminus to avoid the connecting with each other.

The condition of the ligation reaction was:

1 μl Quick ligase (NEB, M2200L), 10 μl 2× Quick ligation buffer, 8.4 μl suspension of magnetic beads attached with extension product and 0.6 μl 10 mM adapter were mixed, and the reaction was performed at 4° C. overnight (about 15 hours). The ligation product was washed with 100 μl 1×B&W buffer for one time, with 150 μl EBT buffer for three times, and the beads were resuspended by 30 μl water containing 0.02% Triton X-100, vibrated at 1400 rpm (10 sec on, 10 sec off), and the elution was performed at 65° C.

The reaction system and condition of the ligation reaction was summarized in below table:

| reagent | volume(μl) |
|---|---|
| the following reaction system was prepared on ice | |
| EB buffer suspension containing magnetic beads attached with DNA | 8.4 |
| 10 mM adapter | 0.6 |
| 2x quick ligation buffer | 10 |
| Quick T4 ligase | 1 |
| total volume | 20 |
| Incubate at 4° C. overnight (14 to 20 hours) And room temperature for 10 min Washing and elution | |
| Washing buffer (1x B&W) | 100 (×1) |
| Washing buffer(EBT) | 150 (×3) |
| Elution buffer (H2O + 0.02% triton) | 30 |
| 1400 rpm vibrating (10" on 10" off), 65° C. heating for 30 min Transferring supernatant to clean PCR tube for the following PCR reaction | |

4.1.4 PCR (Amplification): Ligating an Adapter Sequence to Both Terminuses of DNA by Two-Step PCR Reaction A. The First PCR Reaction System

| reagent | volume(μl) |
|---|---|
| DNA (in water) | 30 |
| 10x EX buffer | 4 |
| 2.5 mM dNTP mix | 3.2 |
| 20 μM P1_FL | 1.2 |
| 20 μM MP24_G5 | 1.2 |
| EX Taq HS polymerase | 0.4 |
| total volume | 40 |
| The procedure was performed in PCR machine: 95° C. 3', (95° C. 30", 60° C. 30", 72° C. 2') x14~19 c, 72° C. 7' Purifying DNA using a Minelute column and eluting the DNA in 25 μl EB buffer | |

For further improve the throughput of the sequencing, several different indexes were introduced via a second PCR, then a standard sequencing library for Illumina sequencing method was constructed.

B. The Second PCR Reaction System

| reagent | volume (μl) |
|---|---|
| Product of first PCR | 4 |
| water | 10.2 |
| 10x EX buffer | 2 |
| 2.5 mM dNTP mix | 1.6 |
| 20 μM P1_sh | 1 |
| 20 μM Index (#1~12) | 1 |
| EX Taq HS polymerase | 0.2 |
| total volume | 20 |
| The procedure was performed in PCR machine: 95° C. 3', (95° C. 30", 55° C. 30", 72° C. 2') x5~7 c, 72° C. 7' 2% agrose gel, 1x TAE, 90 V, electrophoresis 24 min Recovering 200-500 bp fragment, finally in 30 μl EB buffer | |

Example 2 RNA-Seq (cDNA Sequencing)

This example was performed in a way similar with Example 1, with the differences were:

Total RNA of a cell was extracted with TRIzol reagent (Invitrogen), and purified with microPoly(A) Purist Kit (Ambion, AM1919), and remaining DNA was digested with DNase I, then the total RNA was subjected to reverse transcription using Poly-T primer (T18) and M-MLV Reverse Transcriptase (Invitrogen). Fragments with suitable length were obtained by ultrasonic fragmentation, and RNase A was used to digest RNA template, and purifying the remaining cDNA strand. The obtained single-stranded cDNA may be used to construct sequencing library according to Example 1 (For single-stranded DNA, may be started form the step of forming tail), and the specificity may be maintained Example 3 ChIP-Seq (Chromatin Immunoprecipitation)

This example was performed in a way similar with Example 1, with the differences were:

The cell used for ChIP was crosslinked in 1% formaldehyde at 37° C. for 10 min, and chromatin was released by lysing the cell. Fragments with length of 200~500 bp were obtained by ultrasonic fragmentation. For each ChIP reaction, 2-5 μg corresponding antibody was added, and incubate at 4° C. overnight. Finally, enriched double-stranded DNA fragments was obtained and after quantification using Qubit, a certain amount of DNA was used to construct sequencing library according to Example 1, and the result showed that the method may be used to construct sequencing library based on about 25 pg-1 ng DNA.

Example 4 Whole-Genome Methyl-Seq (Methylation Sequencing)

1. Extraction of Cell Whole Genomic DNA

Firstly, cells with good growth condition was picked up by micromanipulation, and was placed in a clean PCR tube with the volume of liquid in the PCR not more than 0.5 μl to extract whole genomic DNA. 20 μl Cell Lysis buffer (Qiagen, 158908) was added to the PCR tube, and RNase A (Roch, 10109169001) was added at a mass volume ratio of 1:30, mixed and incubate overnight at 37° C. Next day, Protein Precipitate buffer (Qiagen, 158912) was added to the system at a volume ratio of 1:3, and vibrated for 20 s and DNA was eluted from protein, and centrifuged at 14000 rpm under room temperature for 10 min, and placed on ice for 5 min, and white protein pellet was formed at bottom of tube, while the DNA was maintained in supernatant. 20 μl isopropanol was added and mixed the tube until no more floccule was formed. Small amount of RNA-Free glucogen was added to locate DNA. Then centrifuged at 14000 rpm under room temperature for 10 min, and DNA will formed at bottom of tube in white or semitransparency. Removing supernatant, and 80% ethanol solution was added to wash the pellet, then centrifuged at 14000 rpm under room temperature for 5 min Repeated washing with 80% ethanol solution, and the pellet was dried under room temperature for several minutes, 20 μl deionized water was used to form a DNA solution.

2. Transforming the Unmethylated Cytimidine Using Bisulfite

For the 20 μl DNA solution, 130 μl bisulfite reagent (EZ DNA Methylation-Direct TM Kit, D5020) was used, and 1:200 λDNA was used to determine the methylation efficiency. The reaction condition was: 98° C. 8 min, 64° C. 3.5 h. The reaction product was reserved at 4° C. for up to 20 hours. To a purification column, 600 μl M-Binding buffer was added and a reaction product of previous step was then added, and centrifuged after mixing. 100 μl M-Wash buffer was used to wash for one time, and to the column 200 μl M-Desulphonation buffer was added and carried out the reaction at room temperature for 15-20 min After the reaction, supernatant was removed by centrifuging, and washed using 200 μl M-Wash buffer for two times. After drying, 10 μl Elution buffer and 40 μl deionized water was used to elute DNA, and a final 50 μl DNA solution was formed, in which the DNA was in a form of single-stranded.

3. Covaris Ultrasonic Fragmentation of DNA

Transferring 50 μl DNA solution of previous step to a Covaris tube, and subjected to ultrasonic shearing:

|  | Target peak (bp) | | | | | | | |
| --- | --- | --- | --- | --- | --- | --- | --- | --- |
|  | 150 | 200 | 250 | 300 | 350 | 400 | 500 | 800 |
| Energy (W) | 50 | 50 | 50 | 50 | 50 | 50 | 50 | 50 |
| Loading | 20% | 20% | 20% | 20% | 20% | 20% | 20% | 20% |
| Pulse cycle | 200 | 200 | 200 | 200 | 200 | 200 | 200 | 200 |
| Treatment time(s) | 375 | 175 | 120 | 80 | 65 | 50 | 32 | 25 |
| Temperature (° C.) | 20 | 20 | 20 | 20 | 20 | 20 | 20 | 20 |
| Sample volume (μl) | 50 | 50 | 50 | 50 | 50 | 50 | 50 | 50 |

4. DNA Library was Constructed in a Way Similar with Example 1 with the Differences that:

Index sequence was added in one PCR reaction, and DNA polymerase used in this PCR reaction was KAPA 2G HS, and the PCR reaction condition was listed below:

| reagent | volume(μl) |
| --- | --- |
| DNA (in water) | 30.5 |
| 5x KAPA buffer A | 10 |
| 2.5 mM dNTP mix | 5 |
| 20 μM P1_FL | 2 |
| 20 μM Index(#1~12) | 2 |
| KAPA 2G HS polymerase | 0.5 |
| total volume | 50 |

The following procedure was performed in a PCR machine:
95° C. 3', (95° C. 30", 60° C. 30", 72° C. 2') x10 c, 72° C. 7'
Exo I 37° C. digestion for 50 min, and 72° C. deactivation for 10 min After PCR amplification, 2 μl Exo I and 6 μl 10× Exo I buffer were used to digest remaining primers. Then DNA having a length of 200 to 700 bp with adapter was obtained, and to remove DNA fragments with a length of over 400 bp and the primer dimer formed in PCR, Ampure XP beads was used to screen target fragments with certain length, and the parameters were listed below:

| parameters | | 150 bp | 200bp | 250 bp | 300-400 bp | 500-600 bp | 500-700 bp |
| --- | --- | --- | --- | --- | --- | --- | --- |
|  | Read length | | | | | | |
|  | Fragment length | 270 bp | 320 bp | 400 bp | 400-500 bp | 500-600 bp | 600-800 bp |
| Ratio of Ampure XP Beads added with the original system | First screen | 0.65 | 0.55 | 0.45 | 0.4 | 0.35 | 0.3 |
|  | Second screen | 0.25 | 0.25 | 0.25 | 0.2 | 0.15 | 0.15 |

The finally obtained DNA was eluted in 20 μl deionized water, and 1 μl was diluted in a fold of 100, then determined the molar concentration by using a KAPA Kit for determining the average length by Agilent 2100. The library was tested as success by sequencing on an Illumina sequencing platform.

Example 5 Specific-Region Methyl-Seq

Firstly cell whole genomic DNA was obtained in a way similar with Example 4, and fragmented the DNA into 2.5 to 5 KB. At least 500 ng DNA fragments were used in the hybridization reaction of DNA and probe with concentrating the DNA into 3.4 μl with a concentration of 147 ng/μL. To the DNA solution, 5.6 μL probe mixture specific to target region was used (normally, the probe has a length of 24 bp with biotin as marker), and 40 μL hybridization buffer (100 mM Tris-HCl pH 7.0, 100 mM NaCl) was used.

In a PCR machine, the reaction was performed as followings: 95° C. 5 min, 65° C. 24 h. This reaction may be incubated at 65° C. for up to 72 hours, with ensuring the loss of solution not more than 4 μL. Magnetic streptavidin C1 beads (Invitrogen, 650.01) prewashed with 1× Binding & Wash (B&W) buffer (10 mM Tris-HCl pH 8.0, 0.5 mM EDTA, 1 M NaCl) was used to resuspend the hybridization reaction product, and adjusted the volume using 1× Binding & Wash (B&W) to 200 μL, vibrated at room temperature under 1400 rpm (10 sec on, 10 sec off), and incubated for 30 min After the reaction, beads attached with DNA was washed by 100 μl 1×B&W buffer for one time, and with 150 μl EBT buffer (10 mM Tris-HCl pH 8.0, 0.02% Triton X-100) for three times. Finally, the captured DNA was eluted in 20 μL elution buffer ($H_2O$+0.02% triton).

The DNA enriched by using specific probes was subjected to methylation transformation using bisulfite reagent (EZ DNA Methylation-Direct TM Kit D5020). The obtained DNA fragments have length of 300-500 bp, and then DNA sequencing library was constructed in a way similar with Example I. The library was tested as success by sequencing on an Illumina sequencing platform.

CONCLUSION

A DNA sequencing library may be constructed successfully based on 25 pg-1 ng DNA, which was demonstrated by Examples 1 to 5.

It will be apparent to those skilled in the art that variations and modifications of the present invention may be made without departing from the scope or spirit of the present invention. Therefore, it is to be understood that the invention is not to be limited to the specific embodiments disclosed and that modifications and other embodiments are intended to be included within the scope of the appended claims. Although specific terms are employed herein, they are used in a generic and descriptive sense only and not for purposes of limitation.

What is claimed is:

1. A method for constructing a sequencing library based on a single-stranded DNA molecule, comprising:
   (1) forming a poly(C)$_n$ tail at a 3'-terminus of the single-stranded DNA molecule, to obtain a single-stranded DNA molecule with the poly(C)$_n$ tail with n representing a number of base C, and n being an integer ranging from 5 to 30;
   (2) obtaining a double-stranded DNA molecule by using an extension primer based on the single-stranded DNA molecule with the poly(C)$_n$ tail, with the extension primer comprising a H(G)$_m$ unit at a 3'-terminus thereof, H being base A, base T or base C, m being a number of base G, and m being an integer ranging from 5 to 15; and
   (3) ligating an adapter to one terminus of the double-stranded DNA molecule remote from the H(G)$_m$ unit, and amplifying the resulting ligation product to obtain an amplification product forming the sequencing library.

2. The method of claim 1, wherein the single-stranded DNA molecule has an amount of at least 25 pg.

3. The method of claim 2, wherein the single-stranded DNA molecule has an amount of 25 pg to 1000 pg.

4. The method of claim 1, wherein n is an integer ranging from 15 to 25.

5. The method of claim 4, wherein n is 20.

6. The method of claim 1, wherein poly(C)n tail is formed by using a terminal deoxynucleotidyl transferase.

7. The method of claim 1, wherein in step (2), the double-stranded DNA molecule is obtained by using a KAPA 2G Robust HS.

8. The method of claim 1, wherein m is 9.

9. The method of claim 1, wherein the extension primer has a sequence of SEQ ID NO:1.

10. The method of claim 1, wherein the extension primer comprises a selection marker formed at a 5'-terminus of the extension primer.

11. The method of claim 1, wherein the selection marker is a biotin.

12. The method of claim 11, in step (3), further comprising purifying the resulting ligation product by using a bead specific to the biotin before the amplification.

13. The method of claim 1, wherein step (3) further comprises:
   (3-1) annealing single-stranded nucleic acids having nucleotide sequences of SEQ ID NOs: 2-3 respectively to form a semi-adapter;
   (3-2) ligating the semi-adapter with one terminus of the double-stranded DNA molecule to obtain a double-stranded DNA molecule with the semi-adapter; and
   (3-3) amplifying the double-stranded DNA molecule with the semi-adapter by using nucleotides of SEQ ID NOs: 4-7 as primers.

14. The method of claim 13, wherein in step (3-2), ligating the semi-adapter with one terminus of the double-stranded DNA molecule is performed by using a Rapid DNA ligase.

15. The method of claim 14, wherein in step (3), amplifying the resulting ligation product is performed by using a primer comprising an Index sequence.

16. The method of claim 15, wherein the primer comprising an Index sequence is one selected from a set of indexed-primer consisting of SEQ ID NO: 8-19.

17. A method for determining a sequence data of a target region in a chromatin, comprising:
   subjecting a chromatin to random fragmentation to obtain a chromatin sample with a length ranging from 200 bp to 500 bp;
   subjecting the chromatin sample to a Chromatin Immunoprecipitation to obtain a double-stranded DNA sample by using an antibody specific to the target region;
   subjecting the double-stranded DNA sample to a denaturation treatment to obtain a single-stranded DNA molecule;
   constructing a sequencing library based on the single-stranded DNA molecule by a method according to claim 1;
   sequencing the sequencing library to obtain a sequencing result; and
   determining the sequence data of the target region in the chromatin based on the sequencing result.

18. A method for determining a methylation information in a genome, comprising:
   subjecting at least a part of the genome to a bisulfate treatment to transform an unmethylated cytosine into a uracil and obtain a transformed genome sample;
   subjecting the transformed genome sample to random fragmentation to obtain a double-stranded DNA sample with a length ranging from 200 bp to 500 bp;
   subjecting the double-stranded DNA sample to a denaturation treatment to obtain a single-stranded DNA molecule;
   constructing a sequencing library based on the single-stranded DNA molecule by a method according to claim 1;
   sequencing the sequencing library to obtain a sequencing result; and
   determining the sequence data of the target region in the chromatin based on the sequencing result.

* * * * *

SEQUENCE LISTING

<160> NUMBER OF SEQ ID NOS: 19

<210> SEQ ID NO 1
<211> LENGTH: 34
<212> TYPE: DNA
<213> ORGANISM: Artificial
<220> FEATURE:
<223> OTHER INFORMATION: Primer

<400> SEQUENCE: 1
gtgactggag ttcagacgtg tgctgggggg gggh         34

<210> SEQ ID NO 2
<211> LENGTH: 16
<212> TYPE: DNA
<213> ORGANISM: Artificial
<220> FEATURE:
<223> OTHER INFORMATION: Primer

<400> SEQUENCE: 2
gacgctcttc cgatct         16

<210> SEQ ID NO 3
<211> LENGTH: 32
<212> TYPE: DNA
<213> ORGANISM: Artificial
<220> FEATURE:
<223> OTHER INFORMATION: Primer

<400> SEQUENCE: 3
gatcggaaga gcgtcgtgta gggaaagagt gt         32

<210> SEQ ID NO 4
<211> LENGTH: 29
<212> TYPE: DNA
<213> ORGANISM: Artificial
<220> FEATURE:
<223> OTHER INFORMATION: Primer

<400> SEQUENCE: 4
gtgactggag ttcagacgtg tgctggggg         29

<210> SEQ ID NO 5
<211> LENGTH: 58
<212> TYPE: DNA
<213> ORGANISM: Artificial
<220> FEATURE:
<223> OTHER INFORMATION: Primer

<400> SEQUENCE: 5
aatgatacgg cgaccaccga gatctacact ctttccctac acgacgctct tccgatct         58

<210> SEQ ID NO 6
<211> LENGTH: 20
<212> TYPE: DNA
<213> ORGANISM: Artificial
<220> FEATURE:
<223> OTHER INFORMATION: Primer

<400> SEQUENCE: 6
aatgatacgg cgaccaccga         20

-continued

```
<210> SEQ ID NO 7
<211> LENGTH: 48
<212> TYPE: DNA
<213> ORGANISM: Artificial
<220> FEATURE:
<223> OTHER INFORMATION: Primer
<220> FEATURE:
<221> NAME/KEY: misc_feature
<222> LOCATION: (25)..(30)
<223> OTHER INFORMATION: n is a, c, g, or t

<400> SEQUENCE: 7
caagcagaag acggcatacg agatnnnnnn gtgactggag ttcagacg          48

<210> SEQ ID NO 8
<211> LENGTH: 48
<212> TYPE: DNA
<213> ORGANISM: Artificial
<220> FEATURE:
<223> OTHER INFORMATION: Primer

<400> SEQUENCE: 8
caagcagaag acggcatacg agatcgtgat gtgactggag ttcagacg          48

<210> SEQ ID NO 9
<211> LENGTH: 48
<212> TYPE: DNA
<213> ORGANISM: Artificial
<220> FEATURE:
<223> OTHER INFORMATION: Primer

<400> SEQUENCE: 9
caagcagaag acggcatacg agatacatcg gtgactggag ttcagacg          48

<210> SEQ ID NO 10
<211> LENGTH: 48
<212> TYPE: DNA
<213> ORGANISM: Artificial
<220> FEATURE:
<223> OTHER INFORMATION: Primer

<400> SEQUENCE: 10
caagcagaag acggcatacg agatgcctaa gtgactggag ttcagacg          48

<210> SEQ ID NO 11
<211> LENGTH: 48
<212> TYPE: DNA
<213> ORGANISM: Artificial
<220> FEATURE:
<223> OTHER INFORMATION: Primer

<400> SEQUENCE: 11
caagcagaag acggcatacg agattggtca gtgactggag ttcagacg          48

<210> SEQ ID NO 12
<211> LENGTH: 48
<212> TYPE: DNA
<213> ORGANISM: Artificial
<220> FEATURE:
<223> OTHER INFORMATION: Primer

<400> SEQUENCE: 12
caagcagaag acggcatacg agatcactgt gtgactggag ttcagacg          48

<210> SEQ ID NO 13
<211> LENGTH: 48
```

<212> TYPE: DNA
<213> ORGANISM: Artificial
<220> FEATURE:
<223> OTHER INFORMATION: Primer

<400> SEQUENCE: 13
caagcagaag acggcatacg agatattggc gtgactggag ttcagacg         48

<210> SEQ ID NO 14
<211> LENGTH: 48
<212> TYPE: DNA
<213> ORGANISM: Artificial
<220> FEATURE:
<223> OTHER INFORMATION: Primer

<400> SEQUENCE: 14
caagcagaag acggcatacg agatgatctg gtgactggag ttcagacg         48

<210> SEQ ID NO 15
<211> LENGTH: 48
<212> TYPE: DNA
<213> ORGANISM: Artificial
<220> FEATURE:
<223> OTHER INFORMATION: Primer

<400> SEQUENCE: 15
caagcagaag acggcatacg agattcaagt gtgactggag ttcagacg         48

<210> SEQ ID NO 16
<211> LENGTH: 48
<212> TYPE: DNA
<213> ORGANISM: Artificial
<220> FEATURE:
<223> OTHER INFORMATION: Primer

<400> SEQUENCE: 16
caagcagaag acggcatacg agatctgatc gtgactggag ttcagacg         48

<210> SEQ ID NO 17
<211> LENGTH: 48
<212> TYPE: DNA
<213> ORGANISM: Artificial
<220> FEATURE:
<223> OTHER INFORMATION: Primer

<400> SEQUENCE: 17
caagcagaag acggcatacg agataagcta gtgactggag ttcagacg         48

<210> SEQ ID NO 18
<211> LENGTH: 48
<212> TYPE: DNA
<213> ORGANISM: Artificial
<220> FEATURE:
<223> OTHER INFORMATION: Primer

<400> SEQUENCE: 18
caagcagaag acggcatacg agatgtagcc gtgactggag ttcagacg         48

<210> SEQ ID NO 19
<211> LENGTH: 48
<212> TYPE: DNA
<213> ORGANISM: Artificial
<220> FEATURE:
<223> OTHER INFORMATION: Primer

<400> SEQUENCE: 19
caagcagaag acggcatacg agattacaag gtgactggag ttcagacg                48